(12) United States Patent
Rodriguez-Lafrasse et al.

(10) Patent No.: US 9,381,209 B2
(45) Date of Patent: Jul. 5, 2016

(54) TREATMENT OF SQUAMOUS CELL CARCINOMA WITH HSP27 ANTISENSE OLIGONUCLEOTIDES AND RADIOTHERAPY

(75) Inventors: Claire Rodriguez-Lafrasse, Venissieux (FR); Elie Hadchity, Lyons (FR)

(73) Assignee: The University of British Columbia, Vancouver (CA)

( * ) Notice: Subject to any disclaimer, the term of this patent is extended or adjusted under 35 U.S.C. 154(b) by 1475 days.

(21) Appl. No.: 12/528,118

(22) PCT Filed: Mar. 4, 2008

(86) PCT No.: PCT/CA2008/000419
§ 371 (c)(1),
(2), (4) Date: Aug. 21, 2009

(87) PCT Pub. No.: WO2008/106781
PCT Pub. Date: Sep. 12, 2008

(65) Prior Publication Data
US 2010/0324115 A1 Dec. 23, 2010

Related U.S. Application Data

(60) Provisional application No. 60/893,086, filed on Mar. 5, 2007.

(51) Int. Cl.
A61K 48/00 (2006.01)
A61K 31/712 (2006.01)
A01K 67/027 (2006.01)
A61K 31/7088 (2006.01)
A61K 31/7125 (2006.01)

(52) U.S. Cl.
CPC .......... *A61K 31/712* (2013.01); *A01K 67/0271* (2013.01); *A61K 31/7088* (2013.01); *A61K 31/7125* (2013.01); *A01K 2207/05* (2013.01); *A01K 2227/105* (2013.01); *A01K 2267/0331* (2013.01)

(58) Field of Classification Search
None
See application file for complete search history.

(56) References Cited

U.S. PATENT DOCUMENTS

| | | |
|---|---|---|
| 5,417,978 A | 5/1995 | Tari et al. |
| 5,801,154 A | 9/1998 | Baracchini et al. |
| 5,855,911 A | 1/1999 | Lopez-Berestein et al. |
| 5,891,858 A | 4/1999 | Rubenstein |
| 5,962,262 A | 10/1999 | Hillman et al. |
| 5,998,148 A | 12/1999 | Bennett et al. |
| 6,905,827 B2 | 6/2005 | Wohlgemuth et al. |
| 7,101,991 B2 | 9/2006 | Gleave et al. |
| 2003/0060399 A1 | 3/2003 | Brophy et al. |

FOREIGN PATENT DOCUMENTS

| | | |
|---|---|---|
| EP | 0813872 | 12/1997 |
| WO | 0105435 A2 | 1/2001 |
| WO | 0170976 A2 | 9/2001 |

OTHER PUBLICATIONS

Suzuki et al. (British J Oral & Max Surg. 45 (2007); 123-129).*
Yonekura et al. (Cell Death & Differentiation 2003, 10: 313-322).*
Concannon et al. (Apoptosis 2003; 8: 61-70).*
Oesterreich et al. (Cancer Res 1993; 53: 4443-4448).*
Ciocca et al. (Cell Stress & Chaperones (2005) 10(2): 86-103).*
NCBI Accession No. NM_001541, The role of heat shock protein 27 in bronchiolitis obliterans syndrome after lung transplantation, Mar. 13, 2011.
Tezel et al., The Mechanisms of hsp27 Antibody-Mediated Apoptosis in Retinal Neuronal Cells, The Journal of Neuroscience, 2000, pp. 3552-3562, vol. 10, No. 10.
Yip et al., Combination Bcl-2 Antisense and Radiation Therapy for Nasopharyngeal Cancer, Clinical Cancer Research, 2005, pp. 8131-8144, vol. 11, No. 22.
NCBI Accession No. NM_006308, Mutant small heat shock protein B3 causes motor neuropathy: utility of a candidate gene approach, Mar. 10, 2011.
NCBI Accession No. AB020027, Small Heat Shock Protein 27 (hsp27) Associates With Tubulin/Microtubules in HeLa Cells, 2002.
NCBI Accession No. X54079, cDNA sequence of a human heat shock protein HSP27, Oct. 7, 2008.
NCBI Accession No. NM_001540, Heat-shock protein expression in leukemia, Mar. 13, 2011.
Taylor et al., Antisense oligonucleotides: a systematic high-throughput approach to target validation and gene function determination, DDT, Dec. 1999, pp. 562-567, vol. 4, No. 12.
Lee et al., The Protective Role of HSP90 against 3-Hydroxykynurenine-Induced Neuronal Apoptosis, Biochemical and Biophysical Research Communications, Jun. 2001, pp. 261-267, vol. 284, No. 2.
Aldrian et al., Overexpression of Hsp27 affects the metastatic phenotype of human melanoma cells in vitro, Cell Stress & Chaperones, 2002, pp. 177-185, vol. 7, No. 2.
Jakubowicz-Gil et al., Quercetin, apoptosis, heat shock, Biochemical Pharmacology, 2002, pp. 1591-1595, vol. 64.
Linder et al., Molecular Characterization of a Novel, Developmentally Regulated Small Embryonic Chaperone from Caenorhabditis elegans, The Journal of Biological Chemistry, Nov. 1996, pp. 30158-30166, vol. 271, No. 47.
Fortin et al., Overexpression of the 27 KDA Heat Shock Protein is Associated with Thermoresistance and Chemoresistance But Not With Radioresistance, Int. J. Radiation Oncology Biol. Phys., 2000, pp. 1259-1266, vol. 46, No. 5.
Munoz et al., Squamous cell carcinoma of the prostate: long-term survival after combined chemo-radiation, Radiation Oncology, 2007, vol. 2, No. 15.
Rocchi et al., Heat Shock Protein 27 Increases after Androgen Ablation and Plays a Cytoprotective Role in Hormone-Refractory Prostate Cancer, Cancer Research, 2004, pp. 6595-6602, vol. 64.

(Continued)

*Primary Examiner* — Kimberly Chong
(74) *Attorney, Agent, or Firm* — Larson & Anderson, LLC

(57) ABSTRACT

Squamous cell carcinomas, such as squamous head and neck cancer, are treated with a combination of radio-therapy and a therapeutic agent that reduces the amount of hsp27 in the squamous cancer cells. In specific embodiments, the therapeutic agent that reduces the amount of hsp27 is an antisense oligonucleotide therapeutic agent.

7 Claims, 5 Drawing Sheets

(56) References Cited

OTHER PUBLICATIONS

Carthew R. W., Genes silencing by double-stranded RNA, Current Opinions in Cell Biologym 2001, pp. 244-248, vol. 13.

Garrido et al., HSP27 as a Mediator of Confluence-dependent Resistance to Cell Death Induced by Anticancer Drugsl, Cancer Research, 1997, pp. 2661-2667, vol. 57.

Elbashir et al., Duplexes of 21-nucleotide RNAs mediate RNA interference in cultured mammalian cells, Nature, 2001, pp. 494-498, vol. 411.

Gery et al., Modulation of clonogenicity, growth, and radiosensitivity of three human epidermoid tumor cell lines by a fibroblastic environment, Int. J Radiat Oncol Biol Phys, 1996, Abstract only.

Huot et al., Increased Survival after Treatments with Anticancer Agents of Chinese Hamster Cells Expressing the Human Mr 27,000 Heat Shock Protein, Cancer Research,1991, pp. 5245-5252, vol. 51.

Rocchi et al., Increased Hsp27 after Androgen Ablation Facilitates Androgen-Independent Progression in Prostate Cancer via Signal Transducers and Activators of Transcription 3-Mediated Suppression of Apoptosis, Cancer Research, 2005, pp. 11083-11093, vol. 65, No. 23.

Rodriguez-Lafrasse et al., Temporal relationships between ceramide production, caspase activation and mitochondrial dysfunction in cell lines with varying sensitivity to anti-Fas-induced apoptosis, Biochem. J., 2001, pp. 407-416, vol. 357, Publisher: Biochemical Society, Great Britain.

Bubendorf et al., Hormone Therapy Failure in Human Prostate Cancer: Analysis by Complementary DNA and Tissue Microarrays, Journal of the National Cancer Institute, 1999, pp. 1758-1764, vol. 91, No. 20.

Cornford et al., Heat Shock Protein Expression Independently Predicts Clinical Outcome in Prostate Cancer, Cancer Research, 2000, pp. 7099-7105, vol. 60.

Oesterreich et al., The Small Heat Shock Protein hsp27 is Correlated with Growth and Drug Resistance in Human Breast Cancer Cell Lines, Cancer Research, 1993, pp. 4443-4448, vol. 53.

Richards et al., Effect of Overexpression of the Small Heat Shock Protein HSP27 on the Heat and Drug Sensitivities of Human Testis Tumor Cells, Cancer Research, 1996, pp. 2446-2451, vol. 56.

Rondeaux et al., Effects of Antisense HSP27 Gene Expression in Osteosarcoma Cells, In Vitro Cell Dev. Biol.—Animal, 1997, pp. 655-658, vol. 33.

Wu et al., Expression of the 25-kDa Heat-Shock Protein (HSP27) Correlates with Resistance to the Toxicity of Cadmium Chloride, Mercuric Chloride, cis-Platinum(II)-Diammine Dichloride, or Sodium Arsenite in Mouse Embryonic Stem Cells Transfected with Sense or Antisense HSP27 cDNA, Toxicology and Applied Pharmacology, 1996, pp. 330-339, vol. 141.

Yamamoto et al., Heat shock protein 27 was up-regulated in cisplatin resistant human ovarian tumor cell line and associated with the cisplatin resistance, Cancer Letters, 2001, pp. 173-181, vol. 168.

Database WPI, Section Ch, Week 199737, 1997, Publisher: Derwent Publication Ltd., London, GB, XP002272450.

Garrido et al., Inconstant association between 27-kDa heat-shock protein (Hsp27) content and doxorubicin resistance in human colon cancer cells. The Doxorubicin-protecting effect of HSP27, European Journal of Biochemistry, 1996, pp. 653-659, vol. 237, No. 3, XP001004835.

Gotham et al., Antisense and SirnaTechnologies—SMI Conference, IDRUGS, 2003, pp. 211-214, vol. 6, No. 3, Publisher, Current Drugs LTD., GB, XP008026723.

Morino et al., Specific Regulation of HSPs in Human Tumor Cell Lines by Flavonoids, In Vivo—International Journal of In Vivo Research, 1997, pp. 265-270, vol. 11, No. 3, XP009007378.

Tamm et al., Antisense therapy in oncology: new hope for an old idea?, Lancet, 2001, pp. 489-497, vol. 358, No. 9280, XP004299974.

Stein, The experimental use of antisense oligonucleotides: a guide for the perplexed, The Journal of Clinical Investigarion, 2001, pp. 641-644, vol. 108, No. 5.

Hargis et al., Antisense Hsp27 oligonucleotides sensitize low pH adapted mammalian cells to hyperthermia, Proceedings of the American Association for Cancer Research Annual Meeting 42, Mar. 2001, pp. 728-729.

Norman et al, Anti-sense Inhibition of Small-Heat-Shock-Protein (HSP27) Expression in MCF-7 Mammary-Carcinoma Cells Induces Their Spontaneous Acquisitin of a Secretory Phenotype, Int. J. Cancer, 1999, pp. 574-582, vol. 82.

Aloy et al., Protective Role of Hsp27 Protein Against Gamma Radiation-Induced Apoptosis and Radiosensitization Effects of Hsp27 Gene Silencing in Different Human Tumor Cells, Int. J. Radiation Oncology, Feb. 2008, pp. 543-553, vol. 70, No. 2.

Lo et al., Identification of over-expressed proteins in oral squamous cell carcinoma (OSCC) patients by clinical proteomic analysis, Clinica Chimica Acta, Feb. 2007, pp. 101-107, vol. 376(1-2).

Mese et al., Prognostic significance of heat shock protein 27 (HSP27) in patients with oral squamous cell carcinoma, Oncology Reports, Mar.-Apr. 2002, pp. 341-344, vol. 9(2).

Miyazaki et al., Predictors of Response to Chemo-Radiotherapy and Radiotherapy for Esophageal Squamous Cell Carcinoma, Anticancer Research, Jul.-Aug. 2005, pp. 2749-2756, vol. 25(4).

Teimourian et al., Down-regulation of Hsp27 radiosensitizes human prostate cancer cells, International Journal of Urology, Sep. 2006, pp. 1221-1225, vol. 13(9).

* cited by examiner

TREATMENT OF SQUAMOUS CELL CARCINOMA WITH HSP27 ANTISENSE OLIGONUCLEOTIDES AND RADIOTHERAPY

This application claims the priority benefit of U.S. Provisional Application No. 60/893,086, filed Mar. 5, 2007, which application is incorporated herein by reference for all purposes.

BACKGROUND OF THE INVENTION

This application relates to the treatment of squamous cell carcinomas using a combination of radiation and an agent that inhibits the level of heat shock protein 27 (hsp27) expression.

Squamous cell carcinoma is a cancer that begins in squamous cells—thin, flat cells that look under the microscope like fish scales. Squamous cells are found in the tissue that forms the surface of the skin, the lining of hollow organs of the body, and the passages of the respiratory and digestive tracts. Squamous cell carcinomas may arise in any of these tissues. Thus, some skin cancer, head and neck cancer, lung cancer, mouth cancer, breast, esophageal cancer, and cervical cancer are cancers of squamous cell origin. Although it is rare, primary squamous cell cancer of the prostate may also occur. Treatment for squamous cell cancer may involve treatment with radiation with or without surgical removal of the tumor mass.

Hsp27 is a known inhibitor of apoptotic cell death in various types of cancers, including some squamous cell carcinomas and can act as a means for protecting cells against chemotherapy agents. Huot et al. (1991) Cancer Res. 51: 5245-5252; Oesterreich et al. (1993) The small heat shock protein hsp27 is correlated with growth and drug resistance in human breast cancer cell lines. Cancer Res. 53: 4443-4448; Garrido et al. (1997) Cancer Res. 57: 2661-2667; Yonekura et al., (2003) Cell Death and Differentiation 10, 313-322. On the other hand, it has been reported that there is no correlation between overexpression of hsp27 expression and resistance of squamous cell head and neck cancer to radiotherapy, even though there is a correlation between hsp27 over expression and heat and drug resistance. Fortin et al., (2000) Int. J. Radiation Oncology Biol. Phys. 46: 1259-1266.

U.S. Pat. No. 7,101,991, which is incorporated herein by reference, discloses oligonucleotide therapeutic agents that target hsp27. Reduction in hsp27 expression was shown to reduce progression of non-squamous prostatic tumor cells to androgen independence, and also to enhance to sensitivity of such prostate tumor cells to chemotherapy.

SUMMARY OF THE INVENTION

Notwithstanding the absence of a correlation between hsp27 over-expression and resistance to radiotherapy, it has now been surprisingly found that reduction of hsp27 expression results in increased radio-sensitivity in squamous cell carcinoma. Thus, the present invention provides a method for treatment of squamous cell carcinoma comprising treating a patient diagnosed with a squamous cell carcinoma with a combination of radio-therapy and a therapeutic agent that reduces the amount of hsp27 in the squamous cancer cells. In specific embodiments, the therapeutic agent that reduces the amount of hsp27 is an oligonucleotide therapeutic.

DETAILED DESCRIPTION OF THE INVENTION

Figure 1:
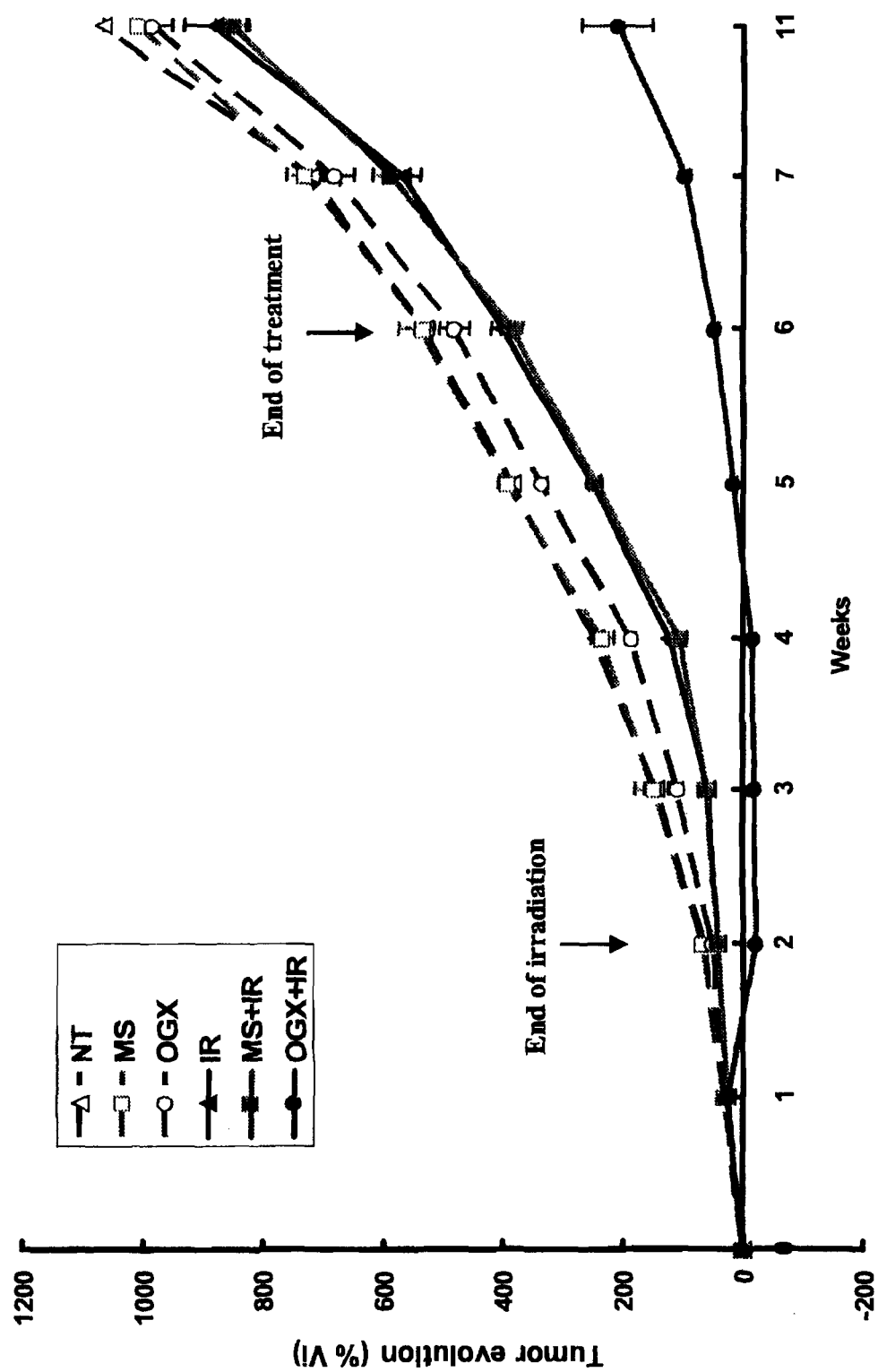
FIG. 1 shows tumor evolution in untreated mice (NT) and in mice treated with the mismatch control oligonucleotide (MS), the hsp27 antisense alone (OGX), radiation alone, 10 Gy (IR), the mismatch control oligonucleotide and radiation 10 Gy (MS+IR) and the hsp 27 antisense and radiation 10 Gy (OGX+IR).

The present invention relates to the use of therapeutic agents that reduce the amount of active hsp27 in squamous cell cancer cells in combination with radio-therapy to provide enhanced therapeutic efficacy to the radio-therapy.

As used in the specification and claims of this application, the term "active hsp27" refers to hsp27 which is active as a chaperone to stabilize protein structure at times of stress and in particular to inhibit the activity of caspase-3, a mediator of apoptosis. Reduction in levels of active hsp27 can be achieved by reducing the total amount of hsp27, either by restricting production of hsp27 or by degrading hsp27 at a rate faster than it is being produced, or by converting hsp27 to an inactive form, for example by sequestering hsp27 in an inactive complex such as with an anti-hsp27 antibody. Anti-hsp27 antibodies are known, for example from Tezel and Wax, *J. Neuroscience* 10:3553-3562 (2000).

The phrase "in combination with radio-therapy" refers to administration of the therapeutic agent that reduces hsp27 at a time before, during or after radiotherapy, provided that the time of administration is sufficiently close to the time of radiotherapy that the reduction in hsp27 overlaps in time with the cytotoxic/apoptotic effects of the radio-therapy.

The sequence of human hsp27 mRNA is known, for example from NCBI Accession Numbers AB020027, X54079, NM_006308, NM_001540 and NM_001541. The cDNA sequence (Seq. ID No. 91) forms the basis for the development of antisense oligonucleotides and RNAi nucleotide inhibitors. Suitable sequences for antisense, and for RNAi are those that target bases in the regions from nucleotides 131-161, 241-261, 361-371, 551-580, 661-681 and 744-764 in Seq. ID No. 91. In order to target bases within these regions, an antisense or RNAi molecule must have sequence specificity with a region that includes at least one of the listed bases, preferably at least 10 of the listed bases. Suitable antisense oligonucleotides have a length of from 12 to 35 oligonucleotides and have sequence specificity to the hsp27 mRNA sequence. Specific suitable antisense sequences are listed with DNA based only in Seq. ID Nos. 1-90. Modifications to include RNA bases in place of the corresponding DNA base may be made.

RNA interference or "RNAi" is a term initially coined by Fire and co-workers to describe the observation that double-stranded RNA (dsRNA) can block gene expression when it is introduced into worms (Fire et al. (1998) Nature 391, 806-811, incorporated herein by reference). dsRNA directs gene-specific, post-transcriptional silencing in many organisms, including vertebrates, and has provided a new tool for studying gene function. RNAi involves mRNA degradation, but many of the biochemical mechanisms underlying this interference are unknown. The use of RNAi has been further described in Carthew et al. (2001) Current Opinions in Cell Biology 13, 244-248, and Elbashir et al. (2001) Nature 411, 494-498, both of which are incorporated herein by reference. The RNAi molecules of the invention are double-stranded or single-stranded RNA of from about 21 to about 23 nucleotides which mediate RNA inhibition. That is, the isolated RNAi of the present invention mediate degradation of mRNA of the hsp27 gene. Specific sequences suitable for use in RNAi inhibitors of hsp27 are listed as Seq. ID Nos. 82-90.

The terms RNA, RNA molecule(s), RNA segment(s) and RNA fragment(s) may be used interchangeably to refer to RNA that mediates RNA interference. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAi compounds are referred to as analogs or analogs of naturally-occurring RNA. RNA of the present invention need only be sufficiently similar to natural RNA that it has the ability to mediate RNAi. As used herein the phrase "mediate RNAi" refers to and indicates the ability to distinguish which mRNA are to be affected by the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or lack of expression of the target mRNA.

Exemplary compositions useful in the invention are antisense hsp27 oligonucleotides or RNAi nucleotide inhibitors as described in U.S. Pat. No. 7,101,991. The invention further relates to the use of these compositions in the treatment of squamous prostate cancer and other squamous cell cancers that express hsp27 in elevated amounts.

The oligonucleotides employed as antisense or RNAi molecules may be modified to increase the stability of the oligonucleotides in vivo. For example, the oligonucleotides may be employed as phosphorothioate derivatives (replacement of a non-bridging phosphoryl oxygen atoms with a sulfur atom) which have increased resistance to nuclease digestion. MOE modification is also effective.

Administration of antisense oligonucleotides can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978 which are incorporated herein by reference. In general, the antisense is administered by intravenous, intraperitoneal, subcutaneous or oral routes, or direct local tumor injection.

The amount of antisense oligonucleotide or other therapeutic administered is one effective to reduce the amount of active hsp 27. It will be appreciated that this amount will vary both with the effectiveness of the antisense oligonucleotides or other therapeutic agent employed, and with the nature of any carrier used. The determination of appropriate amounts for any given composition is within the skill in the art, through standard series of tests designed to assess appropriate therapeutic levels. By way of specific non-limiting example, the 4-12-4 2'-MOE gapmer of Seq ID No. 92 discussed in the examples below is being tested in phase I human clinical trials in combination with docetaxel therapy using weekly injected doses of 200 mg, 400 mg, 600 mg, 800 mg or 1000 mg.

The RNAi molecules of the invention are used in therapy to treat patients, including human patients, that have cancers or other diseases of a type where a therapeutic benefit is obtained by the inhibition of expression of the targeted protein. siRNA molecules of the invention are administered to patients orally, by one or more daily injections (intravenous, subcutaneous, intravesical, or intrathecal) or by continuous intravenous or intrathecal administration for one or more treatment cycles to reach plasma and tissue concentrations suitable for the regulation of the targeted mRNA and protein.

The ability of therapeutic agents that reduce the level of hsp27 to enhance the radio-sensitivity of squamous cell carcinoma was determined in experiments using a radio-resistant human cell line derived from a head and neck squamous cell carcinoma as described in the example below. In these examples, the therapeutic agent is a 4-12-4 2'-MOE gapmer oligonucleotide with phosphorothiolated internucleotide linkages which can be represented as 5'-GGG<u>A</u>MeCGMeCGGMeCGMeCTMeCGG<u>Me</u>U<u>Me</u>C<u>A</u>MeU-3', (Seq. ID No. 92) where G, A, MeC, and T represent the nucleosides 2'-deoxyguanosine, 2'-deoxyadenosine, 2'-deoxy-5-methylcytidine, and 2'-deoxythymidine (DNA nomenclature). The underlined nucleosides (G, A, MeC, and MeU) denote 2'-O-methoxyethyl (2'-MOE) modifications of the nucleosides (RNA nomenclature for guanosine, adenosine, 5-methylcytidine and 5-methyluridine). The internucleotide linkages are phosphothioate diester (sodium salts). This compound is also known by the name OGX-427 and CAS Registry No. 915443-09-3. This oligonucleotide was observed to reduce the amount of hsp27 protein in the cells after treatment with combined oligonucleotide and radiation therapy by over 68% as compared to treatment with radiation and a mismatch oligonucleotide control sequence.

FIG. 1 shows tumor evolution in untreated mice (NT) and in mice treated with the mismatch control oligonucleotide (MS), the hsp27 antisense alone (OGX), radiation alone (IR), the mismatch control oligonucleotide and radiation (MS+IR) and the hsp 27 antisense and radiation (OGX+IR). As is readily apparent, the combination of hsp 27 antisense and radiation resulted in a dramatic change in the rate of tumor evolution.

Figure 2:
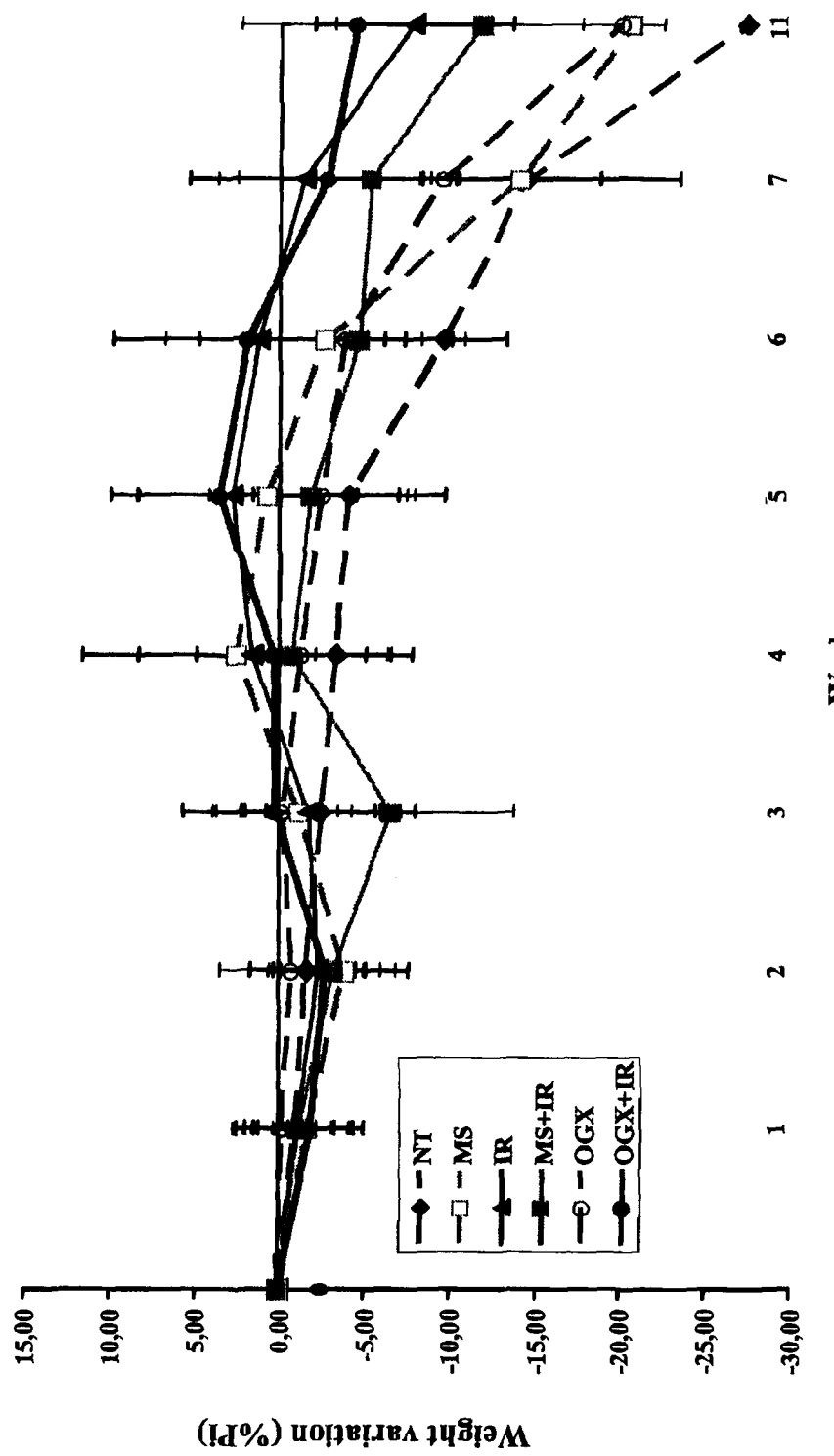
FIG. 2 shows weight variation in the mice of FIG. 1.

No significant additional tissue damage or toxicity (as reflected by weight loss) was observed in mice treated with the antisense oligonucleotide, with or without radiation, as compared to mismatch oligonucleotide treatments. FIG. 2 shows weight variation for the same mice as FIG. 1. This figure shows that minimal variation in weight occurred for the effective treatment regime.

EXAMPLES

Example 1

A) Protocol

Tumor Cell Line

Radioresistant SQ20B human cell line, derived from a head and neck squamous cell carcinoma (HNSCC), established in John Little's laboratory (Department of Cancer Biology, Harvard School of Public Health, Boston, USA) (Gery B et al., (1996). Int J Radiat Oncol Biol Phys 34:

1061-1071). These cells are characterized by a high level of Hsp27 protein expression (1.53 μg/mg total protein). Cells were grown in DMEM-Glutamax I™ medium supplemented with 10% fetal calf serum (Rodriguez-Lafrasse C et al., (2001). Biochem 357:407-416).

Treatment of Cells with Antisense Oligonucleotide

SQ20B cells were plated at the density of 24000 cells per cm² and treated the day after for 1 or 2 days with OGX-427 (OncoGenex Technologies, Inc., Vancouver, Canada) or mismatch control (MS) oligonucleotides at a concentration of 200 nM after a preincubation for 20 minutes with 3.5 mg/ml of OligofectAMINE™ (Invitrogen-Life Technologies, Inc) in serum-free OPTI-MEM™ (Invitrogen). Four hours after the beginning of the incubation, the medium was replaced with standard culture medium.

Western Blot Analysis

Hsp27 protein levels were assessed by Western Blot analysis with a mouse monoclonal anti-Hsp27 (Stressgen). GAPDH was used as a loading control. For densitometric analysis, scanned autoradiographs were quantified using 1Dscan EX3.1 software.

Clonogenic Assay

Clonogenic survival of SQ20B treated cells was assessed by a standard colony-formation assay as described by Alphonse et al. (2004) Oncogene. 23(15):2703-15. Three hours after treatment, cells were harvested and seeded in 25 cm² culture flasks at densities of 16 to 120 cells/cm². Cells were then irradiated with a Clinac 600C™ X-ray irradiator, at doses varying between 0.5 and 8 Gy. The survival variables A and B were plotted according to the linear quadratic equation $(SF=\exp[-A \times D - B \times D^2])$, where D represents the dose of irradiation. The survival fraction at 2 Gy (SF2) was determined as an index of radiosensitivity.

B) Results

Dose-Dependant Inhibition of Hsp27 Expression by OGX-427

SQ20B treated cells were collected at different times after transfection and the decrease of Hsp27 protein expression was measured by Western Blot analysis. OGX-427 treatment dose-dependently inhibited Hsp27 expression, up to 70% for 200 nM treatment and 90% for 2×200 nM at 24 hours post-transfection. MS control oligonucleotide did not modify Hsp27 expression.

OGX-427 Increases Clonogenic Cell Death

To determine whether the attenuation of Hsp27 protein expression sensitizes SQ20B cells to irradiation, survival curves were established after treatment. A significant increase of clonogenic cell death was observed, the survival fraction at 2 Gy (SF2) shifted from 0.72 to 0.49 in SQ20B treated with 2×200 nM OGX-427 (SF2=0.71 in SQ20B MS cells).

Example 2

We next evaluated the effect of OGX-427 treatment in combination to irradiation on SQ20B heterotopic xenograft tumors.

A) Protocol

Approximately $3 \times 10^6$ SQ20B cells diluted in 0.2 ml PBS were subcutaneously inoculated in the right flank region of 4 weeks old female athymic nude mice (SWISS nu/nu) (Charles River, France) via a 23-gauge needle, under ketamine and xylazine anesthesia. When tumors reached 400 to 500 mm3, usually 4 to 5 weeks after injection, mice were randomly divided into six treatment groups:

1—Untreated (10 mice)
2—Radiation alone (10 mice),
3—MS (10 mice),
4—OGX-427 (10 mice),
5—MS+radiation (10 mice),
6—OGX-427+radiation (11 mice).

ASO-Hsp27 (OGX-427) and MS at doses of 10 mg/kg (diluted in PBS) were administered by intraperitoneal injection (3, 4, 5, 6 groups). Mice were treated for six weeks. In the first week, oligonucleotides were injected during 5 consecutive days (from Wednesday to Sunday). The 2, 5, 6 groups of mice were irradiated at a dose of 2 Gy/day (1 Gy from each side of the tumor) for 5 consecutive days (from Monday to Friday) combined to 3 injections of oligonucleotides for the 5, 6 groups (on Monday, Wednesday and Friday, after irradiation). The last four weeks of treatment, 3 injections/week were performed (on Monday, Wednesday and Friday) on 3, 4, 5, 6 groups. Before irradiation on the Clinac X-ray irradiator (Radiotherapy Department of Lyon-Sud Hospital Center), mice were anaesthetized with ketamine (120 mg/kg) and xylazine (10 mg/kg). Tumors were measured once weekly by use of calipers and their volumes were calculated by the formula: 0.5236 a×b2, where a and b are long and short diameters respectively.

The delivered amount of OGX-427 was selected in reference to the works of Rocchi P et al 2004. Cancer Res. 64: 6595-6602, Rocchi P et al 2005. Cancer Res. 65:11083-11093, Yip K W et al 2005. Clin Cancer Res. 11:8131-8144. The radiation dose of 2 Gy per day was chosen as being the therapeutic dose given daily to a patient.

Tumor growth, toxicity (weight) and mortality were followed along the treatment. Apoptosis and Hsp27 protein expression were analyzed on tumors taken after irradiation (at the end of the second week) and at the end of the treatment. Table 1 shows the number of mice sacrificed at each step, and mice death.

Apoptosis was detected using TUNEL staining (Promega), and Hsp27 protein level was determined by Western Blot analysis.

B) Results

Effects of OGX-427 Combined to Irradiation on SQ20B Tumor Growth

Tumor evolution was represented by the percentage of initial tumor volume at the beginning of treatment. Table 2 shows the number of mice used for measurement of tumor volume in each week of the experiment. The results of these measurements are summarized in FIG. 1.

TABLE 1

|  | After irradiation (end 2$^{nd}$ week) | End of treatment (end 6$^{th}$ week) | Mortality 17 weeks following treatment |
|---|---|---|---|
| Untreated (10 mice) | 4 | 2 | 4* |
| Radiation alone (10 mice) | 3 | 2 | 1" |
|  |  |  | 4* |
| MS (10 mice) | 4 | 2 | 4* |

TABLE 1-continued

|  | After irradiation (end $2^{nd}$ week) | End of treatment (end $6^{th}$ week) | Mortality 17 weeks following treatment |
|---|---|---|---|
| OGX-427 (10 mice) | 3 | 2 | 5* |
| MS + radiation (10 mice) | 3 | 2 | 1", 4* |
| OGX-427 + radiation (11 mice) | 3 | 2 | 1", 3* |

*Natural death (during treatment)
"Death due to anaesthesia

TABLE 2

| Mice* | Week | | | | | | | |
|---|---|---|---|---|---|---|---|---|
|  | 1 | 2 | 3 | 4 | 5 | 6 | 7 | 11 |
| NT | 10 | 10 (4) | 6 | 5 | 5 | 5 (2) | 3 | 1 |
| MS | 10 | 10 (4) | 6 | 5 | 5 | 5 (2) | 3 | 1 |
| OGX | 9 | 9 (3) | 6 | 6 | 6 | 6 (2) | 4 | 3 |
| IR | 10 | 9 (3) | 6 | 6 | 6 | 6 (2) | 4 | 4 |
| MS + IR | 9 | 8 (3) | 5 | 4 | 4 | 4 (2) | 2 | 2 |
| OGX + IR | 11 | 10 (3) | 7 | 7 | 6 | 6 (2) | 3 | 3 |

Table 2 shows number of mice on which the measurement of tumor volume was taken.
(number) of sacrificed mice at the end of week 2 and 6.

In vivo, OGX-427 monotherapy had no effect on tumor evolution (same slope as non-treated and MS mice). Irradiation alone and MS+irradiation induced a tumor regression on the second and third week of treatment. From the fourth week, the curve of tumor evolution paralleled that of non-treated mice. Combining OGX-427 treatment with radiotherapy inhibited tumor growth very significantly. At the end of treatment (week 6), the tumor volume began to increase. Apoptosis was evaluated on tumor taken at the end of the second week of treatment by the TUNEL immuno-staining. Apoptosis was significantly increased in tumors from mice treated by OGX-427+IR, as compared to MS or MS+IR.

To determine the level of Hsp27 protein decrease induced by OGX-427, Western blots were performed on tumors taken at the end of the second week of treatment. Hsp27 was significantly decreased in OGX-treated tumors, up to 65% compared to MS-treated tumors.

No significant tissue damage, toxicities (weight loss) were observed on mice treated with OGX-427 combined or not with irradiation, compared to MS-treated groups as reflected in FIG. 2. Two mice which received the combined treatment (OGX+IR) were still alive at week 17, while all the mice from the other groups (untreated, IR, MS, MS+IR and OGX mice) died on weeks 13-14.

Example 3

In the study reported in Example 2, we observed the sensitization of OGX-427 treatment on HNSCC xenograft tumors irradiated with a total dose of 10 Gy. In order to confirm the effect of OGX-427 combined to irradiation, a second in vivo study was performed. Mice received the same OGX-427 treatment but were irradiated for a total dose of 30 Gy. In the absence of significant difference in the evolution of tumors from mice treated with MS-control alone or associated with irradiation observed in Example 2, this study was only conducted in three groups of mice: Untreated, Radiation 30 Gy, and OGX-427+30 Gy.
A) Experimental Protocol Female athymic nude mice (Charles River, France) were injected s.c with 3×106 of SQ20B cells in the right flank region via a 23-gauge needle under ketamine/xylazine anesthesia. When tumors reached a volume of 300 to 400 mm3, usually 5 to 6 weeks after injection, mice were randomly divided into three treatment groups (16 mice/group): Untreated, Radiation 30 Gy, OGX-427+radiation 30 Gy. Mice received the same OGX-427 (10 mg/kg for six weeks) treatment as in the first study. Tumors were irradiated for a total dose of 30 Gy delivered at a dose of 2 Gy/day (5 days/week) (weeks 2, 3, 4) (dose rate of 2 Gy/min). Irradiations were performed with a Saturn 42 irradiator, under ketamine/xylazine anesthesia.

Figure 3:
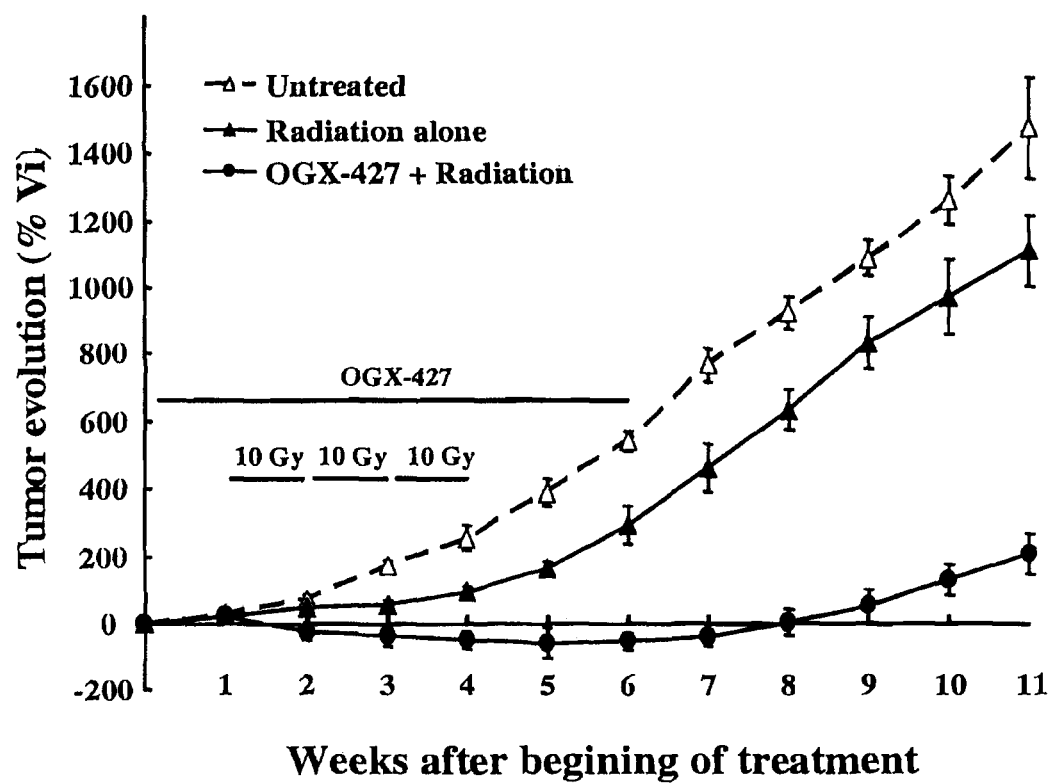
FIG. 3 shows tumor evolution as the percentage of initial tumor volume at the beginning of treatment (Vi) when mice are treated with OGX-427 and radiation at a level of 30 Gy.

Mice were monitored by general clinical observation as well as by body weight and tumor growth. Assessment of tumor volume was followed up weekly over 11 weeks from the beginning of the treatment and was calculated according to the formula: $0.5236 \, (L \times W2)$, where (L) and (W) are the length and width diameters, respectively. Histological analysis and quantifications of biochemical markers were performed on tumors taken after irradiation and at the end of treatment.
B) Results OGX-427 Combined to 30 Gy Significantly Inhibits SQ20B Tumor Growth Tumor evolution was represented by the percentage of initial tumor volume at the beginning of treatment (Vi) and the results are summarized in FIG. 3. Combining OGX-427 treatment with 30 Gy radiation significantly increased the inhibition of tumor growth. At the end of treatment, a respective 720 and 500% reduction of mean tumor volume was measured compared to the non-treated and only irradiated mice groups.

Combined Treatment of OGX-427 and Radiation Enhances Apoptosis and Decreases Cell Proliferation Immunohistochemical analyses showed higher levels of apoptosis (TUNEL staining) and a decrease of tumor cell proliferation (Ki-67 staining) in tumors from mice treated with OGX-427 plus radiation. An amplification of the level of apoptosis by increasing the dose of radiation without changing OGX-427 treatment was also observed. In the same way, a greater decrease in cell proliferation was observed in tumors treated with OGX-427 combined with 30 Gy irradiation (Ki-67 positive cells).

Figure 4:
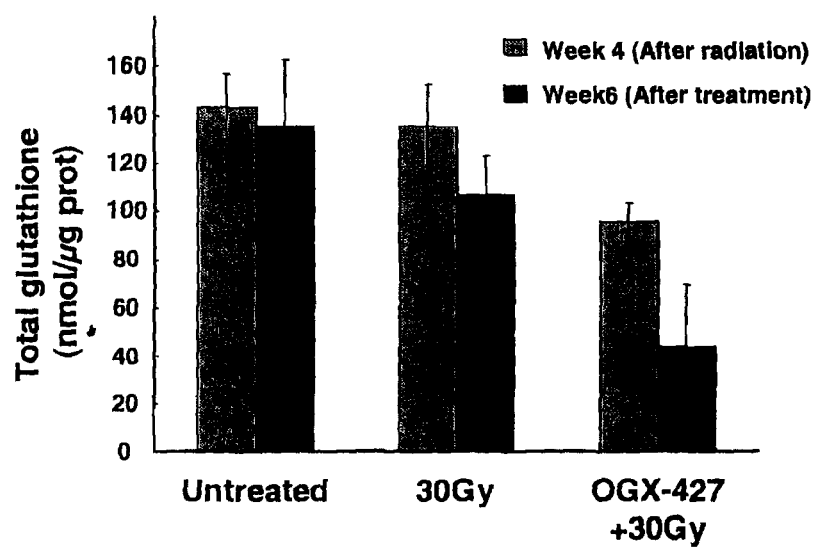
FIG. 4 shows glutathione levels in mice treated with OGX-427 and radiation at a level of 30 Gy.

The increase of apoptosis was associated with an attenuation of the antioxidant defense capacity of tumor cells. OGX-427 combined with 30 Gy irradiation decreases significantly the intratumoral glutathione levels. As reflected in FIG. 4, at the end of treatment (week 6), glutathione level decreased respectively of 68 and 59% compared to non-treated and irradiated mice groups.

Combined Treatment Had No Significant Impact on Host Toxicity

Figure 5B:
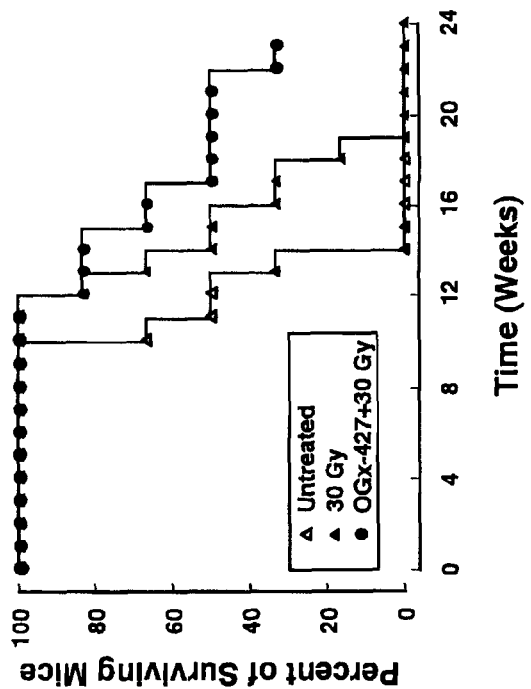
FIGS. 5A and 5B show the host toxicity profile of radiation therapy, as monitored by body weight measurements in tumor-bearing mice and survival percentage, respectively.
Figure 5A:
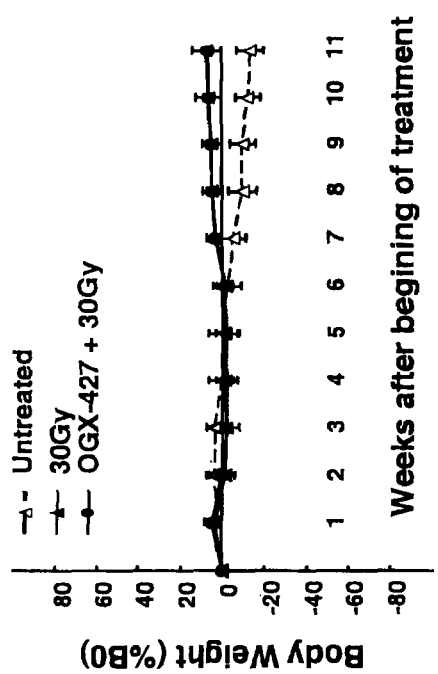

OGX-427 did not significantly alter the host toxicity profile of radiation therapy, as monitored by body weight measurements in tumor-bearing mice (See. FIGS. 5A and B). No significant tissue damage (liver, brain) was observed in mice receiving combined treatment. The absence of toxicity was also confirmed by the increased survival in the group of mice treated with OGX-427 plus radiation as compared with control mice.

These results confirm those obtained in the study of Example 2. Increasing dose of tumor radiation (30 Gy) in combination with OGX-427 treatment significantly amplifies the inhibition of tumor growth, the increase of apoptosis and the decrease of tumor cell proliferation. In addition, we observed a significant decrease of the intratumoral level of glutathione, an antioxidant protector.

The invention claimed is:

1. A method for treatment of squamous cell carcinoma characterized by elevated expression of hsp27 as compared to non-cancerous cells of the same type in an individual suffering from the cancer, comprising treating a patient diagnosed with a squamous cell carcinoma with a combination of radiotherapy and a therapeutic agent that reduces the amount of hsp27 in the squamous cancer cells, wherein the therapeutic agent that reduces the amount of hsp27 is an antisense oligonucleotide therapeutic.

2. The method of claim 1, wherein the oligonucleotide comprises Seq. No. 82.

3. The method of claim 2, wherein the oligonucleotide is a 4-12-4 2'-MOE gapmer oligonucleotide with phosphorothiolated internucleotide linkages which can be represented as 5'-GGGAMeCGMeCGGMeCGMeCTMeCGG MeUMeCAMeU-3'(Seq. ID No. 92) where G, A, MeC, and T represent the nucleosides 2'-deoxyguanosine, 2'-deoxyadenosine, 2'-deoxy-5-methylcytidine, and 2'-deoxythymidine, the underlined nucleosides denote 2'-O-methoxyethyl (2'-MOE) modifications of the nucleosides, and the internucleotide linkages are phosphothioate diester, sodium salts.

4. The method of claim 3, in which the squamous cell carcinoma is head and neck cancer.

5. The method of claim 1, in which the squamous cell carcinoma is head and neck cancer.

6. The method of claim 2, in which the squamous cell carcinoma is head and neck cancer.

7. The method of claim 1, wherein the squamous cell carcinoma is squamous cell skin cancer, squamous cell lung cancer, squamous cell breast cancer, squamous cell esophageal cancer, or squamous cell cervical cancer.

* * * * *

SEQUENCE LISTING

```
<160> NUMBER OF SEQ ID NOS: 92

<210> SEQ ID NO 1
<211> LENGTH: 21
<212> TYPE: DNA
<213> ORGANISM: Homo sapiens

<400> SEQUENCE: 1
gctgactctg ctcctcgtgc c                                              21

<210> SEQ ID NO 2
<211> LENGTH: 21
<212> TYPE: DNA
<213> ORGANISM: Homo sapiens

<400> SEQUENCE: 2
ggtcatgctg gctgactctg c                                              21

<210> SEQ ID NO 3
<211> LENGTH: 21
<212> TYPE: DNA
<213> ORGANISM: Homo sapiens

<400> SEQUENCE: 3
cgcggcgctc ggtcatgctg g                                              21

<210> SEQ ID NO 4
<211> LENGTH: 21
<212> TYPE: DNA
<213> ORGANISM: Homo sapiens

<400> SEQUENCE: 4
gagaagggga cgcggcgctc g                                              21

<210> SEQ ID NO 5
<211> LENGTH: 21
<212> TYPE: DNA
<213> ORGANISM: Homo sapiens

<400> SEQUENCE: 5
ccgcaggagc gagaagggga c                                              21

<210> SEQ ID NO 6
<211> LENGTH: 21
<212> TYPE: DNA
<213> ORGANISM: Homo sapiens

<400> SEQUENCE: 6
agctggggcc ccgcaggagc g                                              21

<210> SEQ ID NO 7
<211> LENGTH: 21
<212> TYPE: DNA
<213> ORGANISM: Homo sapiens

<400> SEQUENCE: 7 aagggggtccc agctggggcc c                                              21
```

```
<210> SEQ ID NO 8
<211> LENGTH: 21
<212> TYPE: DNA
<213> ORGANISM: Homo sapiens

<400> SEQUENCE: 8
ccagtcgcgg aaggggtccc a                                              21

<210> SEQ ID NO 9
<211> LENGTH: 21
<212> TYPE: DNA
<213> ORGANISM: Homo sapiens

<400> SEQUENCE: 9
tatgcgggta ccagtcgcgg a                                              21

<210> SEQ ID NO 10
<211> LENGTH: 21
<212> TYPE: DNA
<213> ORGANISM: Homo sapiens

<400> SEQUENCE: 10
aagaggcggc tatgcgggta c                                              21

<210> SEQ ID NO 11
<211> LENGTH: 21
<212> TYPE: DNA
<213> ORGANISM: Homo sapiens

<400> SEQUENCE: 11
ggcctggtcg aagaggcggc t                                              21

<210> SEQ ID NO 12
<211> LENGTH: 21
<212> TYPE: DNA
<213> ORGANISM: Homo sapiens

<400> SEQUENCE: 12
gcagcccgaa ggcctggtcg a                                              21

<210> SEQ ID NO 13
<211> LENGTH: 21
<212> TYPE: DNA
<213> ORGANISM: Homo sapiens

<400> SEQUENCE: 13
ggcagccggg gcagcccgaa g                                              21

<210> SEQ ID NO 14
<211> LENGTH: 21
<212> TYPE: DNA
<213> ORGANISM: Homo sapiens

<400> SEQUENCE: 14
ccactcctcc ggcagccggg g                                              21

<210> SEQ ID NO 15
<211> LENGTH: 21
<212> TYPE: DNA
<213> ORGANISM: Homo sapiens

<400> SEQUENCE: 15
accactgcga ccactcctcc g                                              21
```

```
<210> SEQ ID NO 16
<211> LENGTH: 21
<212> TYPE: DNA
<213> ORGANISM: Homo sapiens

<400> SEQUENCE: 16
ctgccgccta accactgcga c                                              21

<210> SEQ ID NO 17
<211> LENGTH: 21
<212> TYPE: DNA
<213> ORGANISM: Homo sapiens

<400> SEQUENCE: 17
tggccagctg ctgccgccta a                                              21

<210> SEQ ID NO 18
<211> LENGTH: 21
<212> TYPE: DNA
<213> ORGANISM: Homo sapiens

<400> SEQUENCE: 18
gcacgtagcc tggccagctg c                                              21

<210> SEQ ID NO 19
<211> LENGTH: 21
<212> TYPE: DNA
<213> ORGANISM: Homo sapiens

<400> SEQUENCE: 19 ggcaggggc gcacgtagcc t                                               21

<210> SEQ ID NO 20
<211> LENGTH: 21
<212> TYPE: DNA
<213> ORGANISM: Homo sapiens

<400> SEQUENCE: 20
ggcggcgggg ggcaggggc g                                               21

<210> SEQ ID NO 21
<211> LENGTH: 21
<212> TYPE: DNA
<213> ORGANISM: Homo sapiens

<400> SEQUENCE: 21
ggctctcgat ggcggcgggg g                                              21

<210> SEQ ID NO 22
<211> LENGTH: 21
<212> TYPE: DNA
<213> ORGANISM: Homo sapiens

<400> SEQUENCE: 22
gccactgcgg ggctctcgat g                                              21

<210> SEQ ID NO 23
<211> LENGTH: 21
<212> TYPE: DNA
<213> ORGANISM: Homo sapiens

<400> SEQUENCE: 23
```
ggcgggcgcg gccactgcgg g                                              21

<210> SEQ ID NO 24
<211> LENGTH: 21
<212> TYPE: DNA
<213> ORGANISM: Homo sapiens

<400> SEQUENCE: 24
cgcggctgta ggcgggcgcg g                                              21

<210> SEQ ID NO 25
<211> LENGTH: 21
<212> TYPE: DNA
<213> ORGANISM: Homo sapiens

<400> SEQUENCE: 25
cggctgagcg cgcggctgta g                                              21

<210> SEQ ID NO 26
<211> LENGTH: 21
<212> TYPE: DNA
<213> ORGANISM: Homo sapiens

<400> SEQUENCE: 26
gctgagttgc cggctgagcg c                                              21

<210> SEQ ID NO 27
<211> LENGTH: 21
<212> TYPE: DNA
<213> ORGANISM: Homo sapiens

<400> SEQUENCE: 27 agacccgct gctgagttgc c                                               21

<210> SEQ ID NO 28
<211> LENGTH: 21
<212> TYPE: DNA
<213> ORGANISM: Homo sapiens

<400> SEQUENCE: 28
cggatctccg agacccgct g                                               21

<210> SEQ ID NO 29
<211> LENGTH: 21
<212> TYPE: DNA
<213> ORGANISM: Homo sapiens

<400> SEQUENCE: 29
cgcagtgtgc cggatctccg a                                              21

<210> SEQ ID NO 30
<211> LENGTH: 21
<212> TYPE: DNA
<213> ORGANISM: Homo sapiens

<400> SEQUENCE: 30
gccagcggtc cgcagtgtgc c                                              21

<210> SEQ ID NO 31
<211> LENGTH: 21
<212> TYPE: DNA
<213> ORGANISM: Homo sapiens

<400> SEQUENCE: 31

-continued agggacacgc gccagcggtc c					21

<210> SEQ ID NO 32
<211> LENGTH: 21
<212> TYPE: DNA
<213> ORGANISM: Homo sapiens

<400> SEQUENCE: 32
gttgacatcc agggacacgc g					21

<210> SEQ ID NO 33
<211> LENGTH: 21
<212> TYPE: DNA
<213> ORGANISM: Homo sapiens

<400> SEQUENCE: 33
gggcgaagtg gttgacatcc a					21

<210> SEQ ID NO 34
<211> LENGTH: 21
<212> TYPE: DNA
<213> ORGANISM: Homo sapiens

<400> SEQUENCE: 34
agctcgtccg gggcgaagtg g					21

<210> SEQ ID NO 35
<211> LENGTH: 21
<212> TYPE: DNA
<213> ORGANISM: Homo sapiens

<400> SEQUENCE: 35
cttgaccgtc agctcgtccg g					21

<210> SEQ ID NO 36
<211> LENGTH: 21
<212> TYPE: DNA
<213> ORGANISM: Homo sapiens

<400> SEQUENCE: 36
catccttggt cttgaccgtc a					21

<210> SEQ ID NO 37
<211> LENGTH: 21
<212> TYPE: DNA
<213> ORGANISM: Homo sapiens

<400> SEQUENCE: 37
tccaccacgc catccttggt c					21

<210> SEQ ID NO 38
<211> LENGTH: 21
<212> TYPE: DNA
<213> ORGANISM: Homo sapiens

<400> SEQUENCE: 38
gccggtgatc tccaccacgc c					21

<210> SEQ ID NO 39
<211> LENGTH: 21
<212> TYPE: DNA
<213> ORGANISM: Homo sapiens

<400> SEQUENCE: 39
cctcgtgctt gccggtgatc t                                              21

<210> SEQ ID NO 40
<211> LENGTH: 21
<212> TYPE: DNA
<213> ORGANISM: Homo sapiens

<400> SEQUENCE: 40
tcctgccgct cctcgtgctt g                                              21

<210> SEQ ID NO 41
<211> LENGTH: 21
<212> TYPE: DNA
<213> ORGANISM: Homo sapiens

<400> SEQUENCE: 41
gccatgctcg tcctgccgct c                                              21

<210> SEQ ID NO 42
<211> LENGTH: 21
<212> TYPE: DNA
<213> ORGANISM: Homo sapiens

<400> SEQUENCE: 42
gggagatgta gccatgctcg t                                              21

<210> SEQ ID NO 43
<211> LENGTH: 21
<212> TYPE: DNA
<213> ORGANISM: Homo sapiens

<400> SEQUENCE: 43
gtgaagcacc gggagatgta g                                              21

<210> SEQ ID NO 44
<211> LENGTH: 21
<212> TYPE: DNA
<213> ORGANISM: Homo sapiens

<400> SEQUENCE: 44
gtatttccgc gtgaagcacc g                                              21

<210> SEQ ID NO 45
<211> LENGTH: 21
<212> TYPE: DNA
<213> ORGANISM: Homo sapiens

<400> SEQUENCE: 45
ggggcagcgt gtatttccgc g                                              21

<210> SEQ ID NO 46
<211> LENGTH: 21
<212> TYPE: DNA
<213> ORGANISM: Homo sapiens

<400> SEQUENCE: 46
tccacaccgg ggggcagcgt g                                              21

<210> SEQ ID NO 47
<211> LENGTH: 21
<212> TYPE: DNA
<213> ORGANISM: Homo sapiens

```
<400> SEQUENCE: 47
ttgggtgggg tccacaccgg g                                              21

<210> SEQ ID NO 48
<211> LENGTH: 21
<212> TYPE: DNA
<213> ORGANISM: Homo sapiens

<400> SEQUENCE: 48
aggaggaaac ttgggtgggg t                                              21

<210> SEQ ID NO 49
<211> LENGTH: 21
<212> TYPE: DNA
<213> ORGANISM: Homo sapiens

<400> SEQUENCE: 49
ggggacaggg aggaggaaac t                                              21

<210> SEQ ID NO 50
<211> LENGTH: 21
<212> TYPE: DNA
<213> ORGANISM: Homo sapiens

<400> SEQUENCE: 50
tgtgccctca ggggacaggg a                                              21

<210> SEQ ID NO 51
<211> LENGTH: 21
<212> TYPE: DNA
<213> ORGANISM: Homo sapiens

<400> SEQUENCE: 51
ccacggtcag tgtgccctca g                                              21

<210> SEQ ID NO 52
<211> LENGTH: 21
<212> TYPE: DNA
<213> ORGANISM: Homo sapiens

<400> SEQUENCE: 52
atgggggcct ccacggtcag t                                              21

<210> SEQ ID NO 53
<211> LENGTH: 21
<212> TYPE: DNA
<213> ORGANISM: Homo sapiens

<400> SEQUENCE: 53
tagcttgggc atgggggcct c                                              21

<210> SEQ ID NO 54
<211> LENGTH: 21
<212> TYPE: DNA
<213> ORGANISM: Homo sapiens

<400> SEQUENCE: 54
actgcgtggc tagcttgggc a                                              21

<210> SEQ ID NO 55
<211> LENGTH: 21
<212> TYPE: DNA
```

```
<213> ORGANISM: Homo sapiens

<400> SEQUENCE: 55
atctcgttgg actgcgtggc t                                           21

<210> SEQ ID NO 56
<211> LENGTH: 21
<212> TYPE: DNA
<213> ORGANISM: Homo sapiens

<400> SEQUENCE: 56
tgggatggtg atctcgttgg a                                           21

<210> SEQ ID NO 57
<211> LENGTH: 21
<212> TYPE: DNA
<213> ORGANISM: Homo sapiens

<400> SEQUENCE: 57
cgaaggtgac tgggatggtg a                                           21

<210> SEQ ID NO 58
<211> LENGTH: 21
<212> TYPE: DNA
<213> ORGANISM: Homo sapiens

<400> SEQUENCE: 58
gcccgcgact cgaaggtgac t                                           21

<210> SEQ ID NO 59
<211> LENGTH: 21
<212> TYPE: DNA
<213> ORGANISM: Homo sapiens

<400> SEQUENCE: 59
cccaagctgg gcccgcgact c                                           21

<210> SEQ ID NO 60
<211> LENGTH: 21
<212> TYPE: DNA
<213> ORGANISM: Homo sapiens

<400> SEQUENCE: 60
cttctgggcc cccaagctgg g                                           21

<210> SEQ ID NO 61
<211> LENGTH: 21
<212> TYPE: DNA
<213> ORGANISM: Homo sapiens

<400> SEQUENCE: 61
gattttgcag cttctgggcc c                                           21

<210> SEQ ID NO 62
<211> LENGTH: 21
<212> TYPE: DNA
<213> ORGANISM: Homo sapiens

<400> SEQUENCE: 62
agtctcatcg gattttgcag c                                           21

<210> SEQ ID NO 63
<211> LENGTH: 21
```

```
<212> TYPE: DNA
<213> ORGANISM: Homo sapiens

<400> SEQUENCE: 63
acttggcggc agtctcatcg g                                              21

<210> SEQ ID NO 64
<211> LENGTH: 21
<212> TYPE: DNA
<213> ORGANISM: Homo sapiens

<400> SEQUENCE: 64
ctaaggcttt acttggcggc a                                              21

<210> SEQ ID NO 65
<211> LENGTH: 21
<212> TYPE: DNA
<213> ORGANISM: Homo sapiens

<400> SEQUENCE: 65
ggcatccggg ctaaggcttt a                                              21

<210> SEQ ID NO 66
<211> LENGTH: 21
<212> TYPE: DNA
<213> ORGANISM: Homo sapiens

<400> SEQUENCE: 66
agcaggggtg ggcatccggg c                                              21

<210> SEQ ID NO 67
<211> LENGTH: 21
<212> TYPE: DNA
<213> ORGANISM: Homo sapiens

<400> SEQUENCE: 67
cagtggcggc agcaggggtg g                                              21

<210> SEQ ID NO 68
<211> LENGTH: 21
<212> TYPE: DNA
<213> ORGANISM: Homo sapiens

<400> SEQUENCE: 68
gaggcacagc cagtggcggc a                                              21

<210> SEQ ID NO 69
<211> LENGTH: 21
<212> TYPE: DNA
<213> ORGANISM: Homo sapiens

<400> SEQUENCE: 69
ggtggcgggg gaggcacagc c                                              21

<210> SEQ ID NO 70
<211> LENGTH: 21
<212> TYPE: DNA
<213> ORGANISM: Homo sapiens

<400> SEQUENCE: 70
agaacacaca ggtggcgggg g                                              21

<210> SEQ ID NO 71
```

```
<211> LENGTH: 21
<212> TYPE: DNA
<213> ORGANISM: Homo sapiens

<400> SEQUENCE: 71
atgtatcaaa agaacacaca g                                              21

<210> SEQ ID NO 72
<211> LENGTH: 21
<212> TYPE: DNA
<213> ORGANISM: Homo sapiens

<400> SEQUENCE: 72
cagaagataa atgtatcaaa a                                              21

<210> SEQ ID NO 73
<211> LENGTH: 21
<212> TYPE: DNA
<213> ORGANISM: Homo sapiens

<400> SEQUENCE: 73
ttgagaaaaa cagaagataa a                                              21

<210> SEQ ID NO 74
<211> LENGTH: 21
<212> TYPE: DNA
<213> ORGANISM: Homo sapiens

<400> SEQUENCE: 74
tgaactttat ttgagaaaaa c                                              21

<210> SEQ ID NO 75
<211> LENGTH: 21
<212> TYPE: DNA
<213> ORGANISM: Homo sapiens

<400> SEQUENCE: 75
gtggttgctt tgaactttat t                                              21

<210> SEQ ID NO 76
<211> LENGTH: 21
<212> TYPE: DNA
<213> ORGANISM: Homo sapiens

<400> SEQUENCE: 76
caggtggttg ctttgaactt t                                              21

<210> SEQ ID NO 77
<211> LENGTH: 18
<212> TYPE: DNA
<213> ORGANISM: Homo sapiens

<400> SEQUENCE: 77
taggcgggcg cggccact                                                  18

<210> SEQ ID NO 78
<211> LENGTH: 21
<212> TYPE: DNA
<213> ORGANISM: Homo sapiens

<400> SEQUENCE: 78
gatctccacc acgccatcct t                                              21
```

```
<210> SEQ ID NO 79
<211> LENGTH: 21
<212> TYPE: DNA
<213> ORGANISM: Homo sapiens

<400> SEQUENCE: 79
tccgagaccc cgctgctgag t                                              21

<210> SEQ ID NO 80
<211> LENGTH: 21
<212> TYPE: DNA
<213> ORGANISM: Homo sapiens

<400> SEQUENCE: 80
ccgagacccc gctgctgagt t                                              21

<210> SEQ ID NO 81
<211> LENGTH: 21
<212> TYPE: DNA
<213> ORGANISM: Homo sapiens

<400> SEQUENCE: 81
ggggacgcgg cgctcggtca t                                              21

<210> SEQ ID NO 82
<211> LENGTH: 20
<212> TYPE: DNA
<213> ORGANISM: Homo sapiens

<400> SEQUENCE: 82
gggacgcggc gctcggtcat                                                20

<210> SEQ ID NO 83
<211> LENGTH: 19
<212> TYPE: RNA
<213> ORGANISM: Homo sapiens

<400> SEQUENCE: 83
cucugcugcg gggucucgg                                                 19

<210> SEQ ID NO 84
<211> LENGTH: 20
<212> TYPE: RNA
<213> ORGANISM: Homo sapiens

<400> SEQUENCE: 84
gcugcuuuuu ccguuguguc                                                20

<210> SEQ ID NO 85
<211> LENGTH: 19
<212> TYPE: RNA
<213> ORGANISM: Homo sapiens

<400> SEQUENCE: 85
gguuggcgug gugguguuc                                                 19

<210> SEQ ID NO 86
<211> LENGTH: 19
<212> TYPE: RNA
<213> ORGANISM: Homo sapiens

<400> SEQUENCE: 86
gcucguggug cggcugguc                                                 19
```

```
<210> SEQ ID NO 87
<211> LENGTH: 19
<212> TYPE: RNA
<213> ORGANISM: Homo sapiens

<400> SEQUENCE: 87
cgagaucacc aucccaguc                                                19

<210> SEQ ID NO 88
<211> LENGTH: 19
<212> TYPE: RNA
<213> ORGANISM: Homo sapiens

<400> SEQUENCE: 88
guucuccuuc ccugucucc                                                19

<210> SEQ ID NO 89
<211> LENGTH: 21
<212> TYPE: RNA
<213> ORGANISM: Homo sapiens

<400> SEQUENCE: 89
ccuucguguc gcgggcccug c                                             21

<210> SEQ ID NO 90
<211> LENGTH: 19
<212> TYPE: RNA
<213> ORGANISM: Homo sapiens

<400> SEQUENCE: 90
augaccgagc gccgcgucc                                                19

<210> SEQ ID NO 91
<211> LENGTH: 764
<212> TYPE: DNA
<213> ORGANISM: Homo sapiens

<400> SEQUENCE: 91
ggcacgagga gcagagtcag ccagcatgac cgagcgccgc gtccccttct cgctcctgcg    60
gggccccagc tgggacccct ccgcgactg gtaccgcat agccgcctct cgaccaggc     120 cttcgggctg ccccggctgc cggaggagtg gtcgcagtgg ttaggcggca gcagctggcc   180
aggctacgtg cgcccccctgc ccccgccgc catcgagagc cccgcagtgg ccgcgcccgc   240
ctacagccgc gcgctcagcc ggcaactcag cagcggggtc tcggagatcc ggcacactgc   300
ggaccgctgg cgcgtgtccc tggatgtcaa ccacttcgcc ccggacgagc tgacggtcaa   360
gaccaaggat ggcgtggtgg agatcaccgg caagcacgag gagcggcagg acgagcatgg   420
ctacatctcc cggtgcttca cgcggaaata cacgctgccc cccggtgtgg accccaccca   480
agtttcctcc tccctgtccc ctgagggcac actgaccgtg gaggccccca tgcccaagct   540
agccacgcag tccaacgaga tcaccatccc agtcaccttc gagtcgcggg cccagcttgg   600
gggcccagaa gctgcaaaat ccgatgagac tgccgccaag taaagcctta gcccggatgc   660
ccacccctgc tgccgccact ggctgtgcct ccccgccac ctgtgtgttc ttttgataca    720
tttatcttct gttttttctca aataaagttc aaagcaacca cctg                  764

<210> SEQ ID NO 92
<211> LENGTH: 20
<212> TYPE: DNA
<213> ORGANISM: artificial
```

```
<220> FEATURE:
<223> OTHER INFORMATION: antisense targeting human hsp27 -- OGX-427
<220> FEATURE:
<221> NAME/KEY: misc_feature
<222> LOCATION: (1)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: methylated
<220> FEATURE:
<221> NAME/KEY: misc_feature
<222> LOCATION: (7)..(7)
<223> OTHER INFORMATION: methylated
<220> FEATURE:
<221> NAME/KEY: misc_feature
<222> LOCATION: (10)..(10)
<223> OTHER INFORMATION: methylated
<220> FEATURE:
<221> NAME/KEY: misc_feature
<222> LOCATION: (12)..(12)
<223> OTHER INFORMATION: methylated
<220> FEATURE:
<221> NAME/KEY: misc_feature
<222> LOCATION: (14)..(14)
<223> OTHER INFORMATION: methylated
<220> FEATURE:
<221> NAME/KEY: misc_feature
<222> LOCATION: (17)..(18)
<223> OTHER INFORMATION: methylated
<220> FEATURE:
<221> NAME/KEY: misc_feature
<222> LOCATION: (17)..(20)
<223> OTHER INFORMATION: 2'-O-methoxyethyl
<220> FEATURE:
<221> NAME/KEY: misc_feature
<222> LOCATION: (20)..(20)
<223> OTHER INFORMATION: methylated

<400> SEQUENCE: 92
gggacgcggc gctcggucau                                              20
```